US00PP28039P3

(12) United States Plant Patent
Danziger

(10) Patent No.: US PP28,039 P3
(45) Date of Patent: May 16, 2017

(54) ***NEMESIA* PLANT NAMED 'DNESUNSHIN'**

(50) Latin Name: *Nemesia hybrida*
Varietal Denomination: DNESUNSHIN

(71) Applicant: Gavriel Danziger, Moshav Mishmar Hashiva (IL)

(72) Inventor: Gavriel Danziger, Moshav Mishmar Hashiva (IL)

(73) Assignee: Danzlger 'DAN' Flower Farm (IL)

( * ) Notice: Subject to any disclaimer, the term of this patent is extended or adjusted under 35 U.S.C. 154(b) by 105 days.

(21) Appl. No.: 14/545,409

(22) Filed: Apr. 30, 2015

(65) Prior Publication Data

US 2016/0324059 P1 Nov. 3, 2016

(51) Int. Cl.
*A01H 5/02* (2006.01)

(52) U.S. Cl.
USPC ..... Plt./458

(58) Field of Classification Search
USPC ..... Plt./263.1, 458
See application file for complete search history.

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Nemesia* cultivar named 'DNESUNSHIN' is disclosed, characterized by abundant, long lasting yellow flowers. Flowers are self-cleaning and do not fade in color. Plants have a compact growth habit and tolerate high temperatures. The new variety is a *Nemesia*, normally produced as an outdoor garden or container plant.

2 Drawing Sheets

Figure 1:
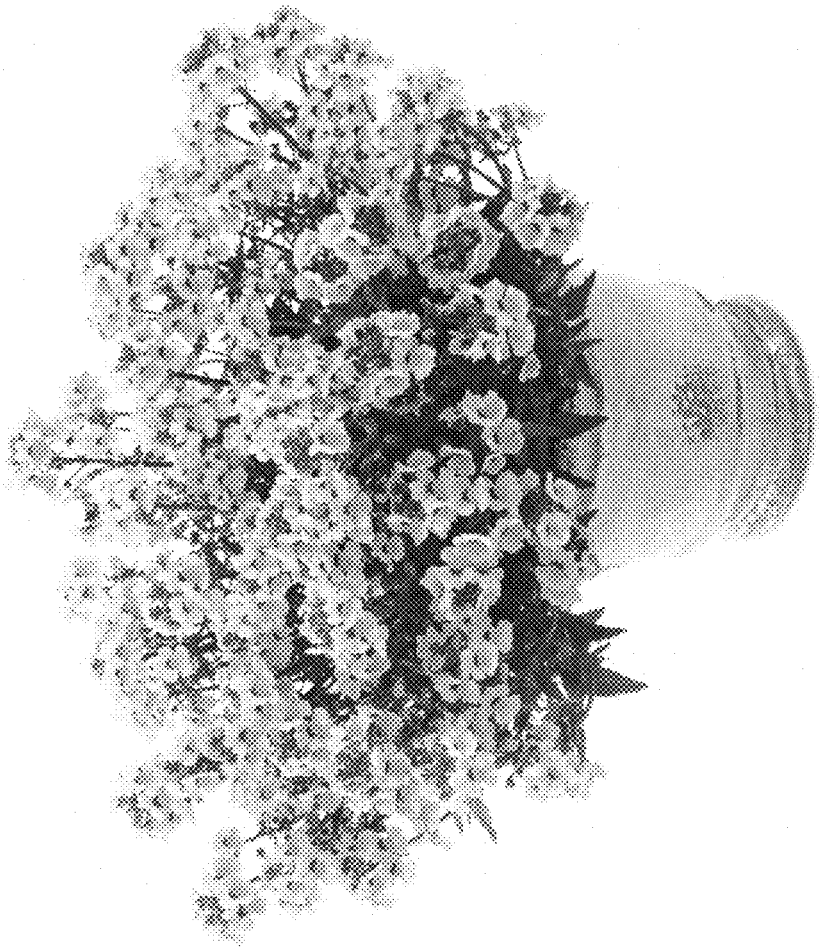

Latin name of the genus and species: *Nemesia hybrida.*
Variety denomination: 'DNESUNSHIN'.

BACKGROUND OF THE INVENTION

The new *Nemesia* cultivar is a product of a planned breeding program conducted by the inventor, Gavriel Danziger, in Moshav Mishmar Hashiva, Israel. The objective of the breeding program was to produce new *Nemesia* varieties for ornamental commercial applications. The cross resulting in this new variety was made during December of 2011.

The seed parent is the, unpatented, proprietary variety referred to as *Nemesia* 'NE-11-1199'. The pollen parent is the unpatented, propriety variety referred to as *Nemesia* 'NE-11-1991'. The new variety was discovered in July of 2012 by the inventor in a group of seedlings resulting from the 2011 crossing, in a research greenhouse in Moshav Mishmar Hashiva, Israel.

Asexual reproduction of the new cultivar was performed by vegetative cuttings. This was first performed at a research greenhouse in Moshav Mishmar Hashiva, Israel in Summer of 2012 and has shown that the unique features of this cultivar are stable and reproduced true to type in multiple successive generations.

SUMMARY OF THE INVENTION

The cultivar 'DNESUNSHIN' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DNESUNSHIN' These characteristics in combination distinguish 'DNESUNSHIN' as a new and distinct *Nemesia* cultivar:

1. Compact growth habit.
2. Long flowering period.
3. Abundance of yellow flowers.
4. Flower color does not fade.
5. Tolerant to high temperatures above 28° C.
6. Self-cleaning flowers.

Plants of the new cultivar 'DNESUNSHIN' are similar to plants of the seed parent, *Nemesia* 'NE-11-1999' in most horticultural characteristics, however, plants of the new cultivar 'DNESUNSHIN' differ in the following;

1. Plants of 'DNESUNSHIN' have yellow flowers, whereas the female parent has light orange and pink-colored flowers
2. The new variety produces smaller flowers.
3. The female parent's foliage reddens in cold temperatures whereas 'DNESUNSHIN' has foliage that remains unchanged (green).
4. The new variety produces more flowers per plant than the seed parent.

Plants of the new cultivar 'DNESUNSHIN' are similar to plants of the pollen parent, *Nemesia* 'NE-11-1991' in most horticultural characteristics, however, plants of the new cultivar 'DNESUNSHIN' differ in the following;

1. Plants of 'DNESUNSHIN' have yellow flowers whereas, male parent variety flowers in shades of light pink.
2. Plants of 'DNESUNSHIN' is well branched in the summer months whereas male parent produces less branches.
3. The new variety produces larger flowers.
4. The new variety has a longer flowering period.
5. The new variety is more vigorous.

COMMERCIAL COMPARISON

Plants of the new cultivar 'DNESUNSHIN' are comparable to the unpatented commercial variety *Nemesia* 'Sunsatia Plus Pera'. The two *Nemesia* varieties are similar in most horticultural characteristics; however, the new variety 'DNESUNSHIN' differs in the following:

1. Earlier flowering.
2. Semi-trailing growth habit. The comparator growth habit is upright.
3. Yellow flowers. The comparator flowers are creamy yellow with lemon yellow eyes.

Plants of the new cultivar 'DNESUNSHIN' can also be comparable to the commercial variety *Nemesia* 'Sunsatia Plus Pomelo', patent status unknown. The two *Nemesia* varieties are similar in most horticultural characteristics; however, the new variety 'DNESUNSHIN' differs in the following:

1. Yellow flowers. The comparator's flowers are honey-yellow in color.
2. Earlier flowering.

BRIEF DESCRIPTION OF THE PHOTOGRAPHS

The accompanying photograph in FIG. 1 illustrates in full color a typical plant of 'DNESUNSHIN' grown in a nursery, in a 13 cm pot. Age of the plant photographed is approximately 12 weeks from a rooted cutting.

Figure 2:
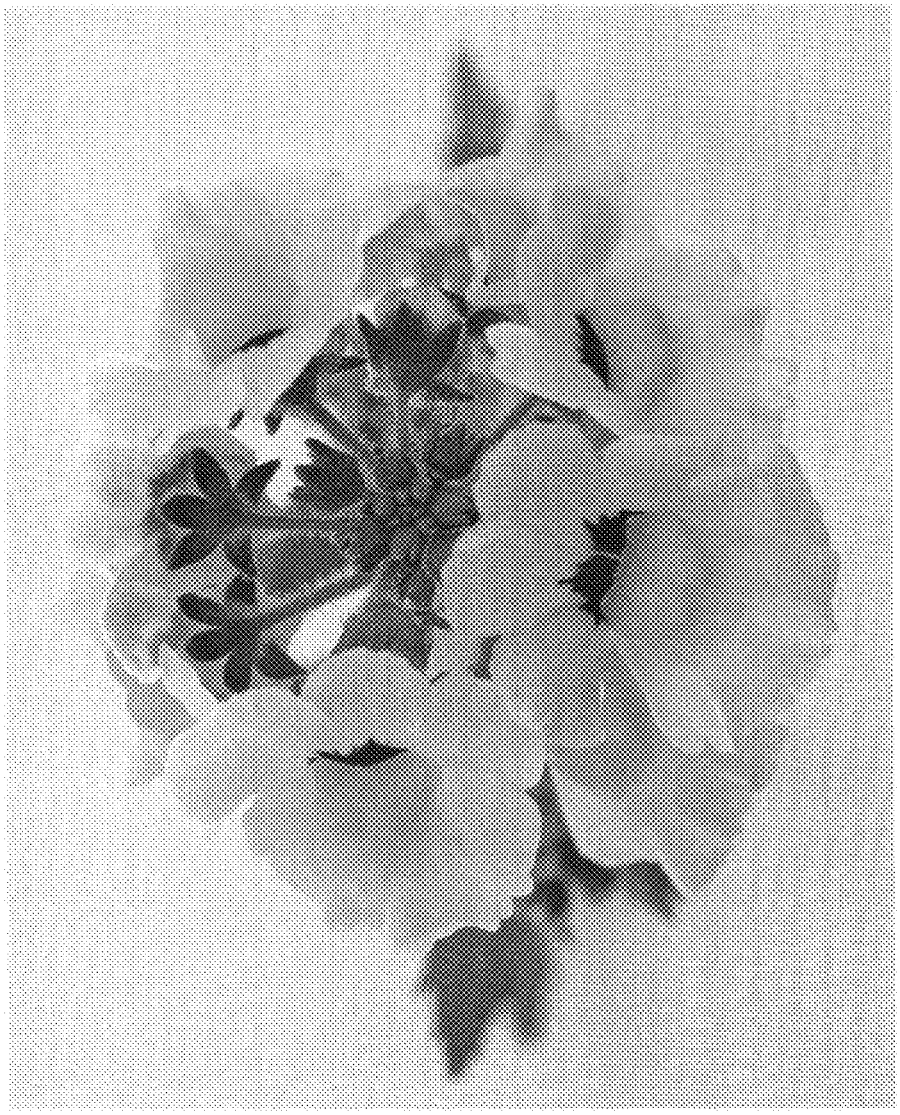

FIG. 2 illustrates a close up of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2001 except where general terms of ordinary dictionary significance are used. The following observations and measurements describe 'DNESUNSHIN' plants grown in the Spring, in a greenhouse, in Moshav Mishmar Hashiva, Israel. The growing temperature ranged from 17° C. to 34° C. during the day and from 10° C. to 14° C. during the night. General light conditions are bright, normal sunlight. Measurements and numerical values represent averages of typical plant types.

Botanical classification: *Nemesia* 'DNESUNSHIN'.

PROPAGATION

Type of propagation typically used: Vegetative terminal cuttings.
Time to initiate roots: 8-13 days.
Root description: Fibrous.

PLANT

Age of plant described: Approximately 80 days from a rooted cutting.
Pot size of plant described: 12 cm.
Growth habit: Semi trailing.
Height: To top of flowers: Approximately 25 cm.
Plant spread: 45 cm.
Growth rate: Fast.
Characteristics of primary lateral branches:
- *Quantity of primary lateral branches.*—5.
- *Length of primary lateral branches.*—20 cm.
- *Form.*—Quadrangular.
- *Diameter.*—0.4 cm.
- *Color.*—RHS Yellow-green 144 A.
- *Texture.*—Smooth.
- *Strength.*—Flexible.

Internode length: 1-2 cm.

FOLIAGE

Leaf:
- *Arrangement.*—Opposite.
- *Quantity.*—Approximately 8 per branch.
- *Average length.*—3.5 cm.
- *Average width.*—1 cm.
- *Shape of blade.*—Lanceolate.
- *Apex.*—Lanceolate.
- *Base.*—Obtuse.
- *Margin.*—Serrate.
- *Texture of top surface.*—Smooth. Texture of bottom surface: Smooth.
- *Pubescence.*—None.
- *Aspect.*—90 degrees to ground.
- *Color.*—Young foliage upper side: RHS Green N 137 A. Young foliage under side: RHS Yellow-green 146 B. Mature foliage upper side: RHS Yellow-green 146 A. Mature foliage under side: RHS Yellow-green 146 D.
- *Venation.*—Type: Pinnate. Venation color upper side: RHS Yellow-green 146 C. Venation color under side: RHS Yellow-green N144 C.
- *Petiole.*—Absent.

FLOWER

Natural flowering season: Autumn/Winter/Spring.
Days to flowering from rooted cutting: 21 days.
Inflorescence and flower type and habit: Raceme.
Rate of flower opening: 4 to 6 days from bud to fully opened flower.
Flower longevity on plant: 7 days.
Approximate quantity of flowers per plant: Per inflorescence, 6 to 12 flowers.
Persistent or self-cleaning: Self-cleaning.
Bud:
- *Shape.*—Obovate.
- *Length.*—0.3 cm.
- *Diameter.*—0.3 cm.
- *Color.*—RHS Yellow-green 144 D.

Corolla:
- *Upper petals* (*upper lip*).—Number: 4. Length: Central petals: 15 mm. Lateral petals: 11 mm. Width: Central petals: 7 mm. Lateral petals: 9 mm. Shape: Obtuse. Aspect: 45 degrees to stem. Margin: Entire. Texture: Smooth. Color: When opening: Upper surface: RHS Green-yellow 1 D. Lower surface: RHS White 155 B. Fully opened: Upper surface: RHS Green-yellow 1 B. Lower surface: RHS White NN155 A.
- *Lower petal* (*lower lip*).—Length: 12 cm. Width: 16 cm. Shape: Cordate. Apex shape: Lobate/obtuse. Color: Upper surface: RHS Yellow 3 A. Lower surface: RHS Green-yellow 1 D.
- *Palate.*—Length: 5 mm. Width: 8 mm. Color: RHS White NN 155 C. Texture: Smooth.

*Throat*.—Length: 9 mm. Color: Near Green-yellow 1 D, blotched Greyed-Purple 187A. Width: 6 mm. Texture: Pubescence. Pubescence: Puberulent.

*Spur*.—Quantity: 1. Length: 1 mm. Diameter: 1 mm. Texture: Pubescence. Color: RHS Greyed-yellow 161 A.

Calyx:

*Form*.—Star-shaped with 5 sepals fused at the base.

*Length*.—3 mm.

*Diameter*.—7 mm.

*Sepal*.—Width: 15 mm. Shape: Cuspidate. Apex: Cuspidate. Margin: Entire. Texture: Pubescent. Color: Upper surface: RHS Green 137 A. Lower surface: RHS Green 137 C.

Pedicel:

*Strength*.—Flexible.

*Aspect*.—45 degree.

*Length*.—20 mm.

*Diameter*.—1 mm.

*Texture*.—Pubescent.

*Color*.—RHS Green 137 C.

*Fragrance*.—Yes, typical Fragrant of *Nemesia*.

REPRODUCTIVE ORGANS

Stamens:

*Number* (*per flower*).—4.

*Filament length*.—0.2 cm.

*Anthers*.—Shape: Oval. Length: 1 mm. Color: RHS Yellow 8 B.

Pollen:

*Color*.—RHS Yellow 7 B.

*Amount*.—Abundant.

Pistils:

*Quantity per flower*.—1.

*Length*.—2 mm.

*Styles*.—Length: 1 mm. Color: RHS Yellow-green 142 D. Stigma: Shape: Oval. Color: RHS yellow-green 142 D.

OTHER CHARACTERISTICS

Seeds and fruits: 5-10 seeds per fruit.

Disease/pest resistance: Neither resistance nor susceptibility to normal diseases and pests of *Nemesia* observed.

Temperature tolerance: Tolerant to high temperatures about 28° C.

What is claimed is:

1. A new and distinct cultivar of *Nemesia* plant named 'DNESUNSHIN' as herein illustrated and described.

* * * * *